(12) United States Patent
Fujiyoshi et al.

(10) Patent No.: US 9,331,119 B2
(45) Date of Patent: May 3, 2016

(54) DETECTION APPARATUS HAVING INTERLAYER INSULATING LAYER COMPOSED OF ORGANIC MATERIAL AND COVERING LAYER COMPOSED OF INORGANIC MATERIAL, DETECTION SYSTEM, AND METHOD FOR PRODUCING DETECTION APPARATUS

(71) Applicant: CANON KABUSHIKI KAISHA, Tokyo (JP)

(72) Inventors: Kentaro Fujiyoshi, Tokyo (JP); Minoru Watanabe, Honjo (JP); Keigo Yokoyama, Honjo (JP); Masato Ofuji, Honjo (JP); Jun Kawanabe, Kumagaya (JP); Hiroshi Wayama, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 132 days.

(21) Appl. No.: 14/041,070

(22) Filed: Sep. 30, 2013

(65) Prior Publication Data

US 2014/0091203 A1    Apr. 3, 2014

(30) Foreign Application Priority Data

Oct. 2, 2012   (JP) ................................ 2012-220385

(51) Int. Cl.
*H01L 21/00*     (2006.01)
*H01L 27/146*    (2006.01)

(52) U.S. Cl.
CPC ........ *H01L 27/14683* (2013.01); *H01L 27/146* (2013.01); *H01L 27/14609* (2013.01); *H01L 27/14663* (2013.01); *H01L 27/14692* (2013.01)

(58) Field of Classification Search
CPC ..................................................... H01L 27/146
USPC ........................... 438/98; 257/431; 250/208.1
See application file for complete search history.

(56) References Cited

U.S. PATENT DOCUMENTS

| | | | | |
|---|---|---|---|---|
| 8,053,269 | B2* | 11/2011 | Tanaka ............................. | 438/69 |
| 8,324,699 | B2* | 12/2012 | Ichijo et al. .................... | 257/431 |
| 8,772,783 | B2* | 7/2014 | Hirosue et al. ................. | 257/72 |
| 8,952,381 | B2* | 2/2015 | Yamazaki ....................... | 257/43 |
| 9,066,035 | B2* | 6/2015 | Kurokawa et al. | |
| 2003/0201447 | A1* | 10/2003 | Yamazaki et al. .............. | 257/79 |
| 2008/0150422 | A1* | 6/2008 | Ohara ........................... | 313/504 |

(Continued)

FOREIGN PATENT DOCUMENTS

| CN | 1945847 A | 4/2007 |
|---|---|---|
| CN | 102222675 A | 10/2011 |

(Continued)

*Primary Examiner* — Caleb Henry
(74) *Attorney, Agent, or Firm* — Canon USA Inc., IP Division

(57) ABSTRACT

A detection apparatus includes a plurality of conversion elements, an interlayer insulating layer, and a covering layer. Each of the plurality of conversion elements includes an electrode electrically connected to a corresponding one of a plurality of switching elements and a semiconductor layer disposed on the electrode. The interlayer insulating layer is disposed so as to cover the plurality of switching elements and composed of an organic material, and has a surface including a first region and a second region located outside the first region. The electrodes are disposed on the surface of the interlayer insulating layer in the first region. The covering layer is disposed on the surface of the interlayer insulating layer in the second region and composed of an inorganic material.

11 Claims, 15 Drawing Sheets

(56) References Cited

U.S. PATENT DOCUMENTS

| | | | |
|---|---|---|---|
| 2008/0180588 A1* | 7/2008 | Ando | 349/37 |
| 2008/0246036 A1* | 10/2008 | Yamazaki et al. | 257/72 |
| 2008/0246064 A1* | 10/2008 | Kimura | 257/292 |
| 2008/0256064 A1 | 10/2008 | Grois | |
| 2008/0283987 A1* | 11/2008 | Kuwabara | 257/678 |
| 2009/0032680 A1* | 2/2009 | Watanabe et al. | 250/208.1 |
| 2011/0226934 A1* | 9/2011 | Tian et al. | 250/208.1 |
| 2012/0139133 A1* | 6/2012 | Takahashi | 257/794 |
| 2012/0305785 A1* | 12/2012 | Fujiyoshi et al. | 250/370.08 |

FOREIGN PATENT DOCUMENTS

| | | |
|---|---|---|
| JP | 2007035773 A | 2/2007 |
| JP | 2008-244445 A | 10/2008 |
| JP | 2009-267326 A | 11/2009 |

* cited by examiner

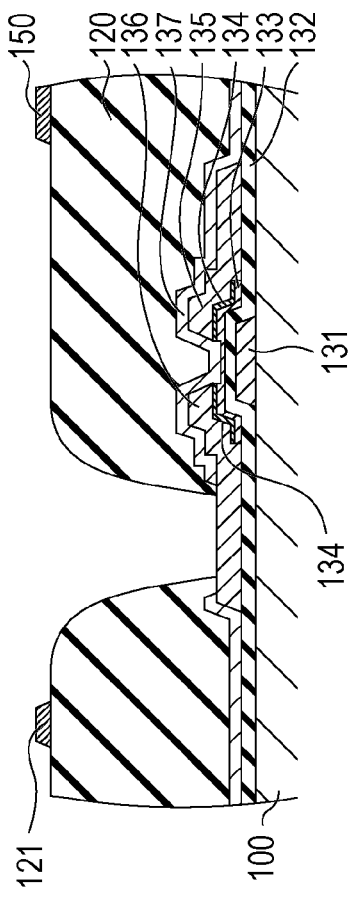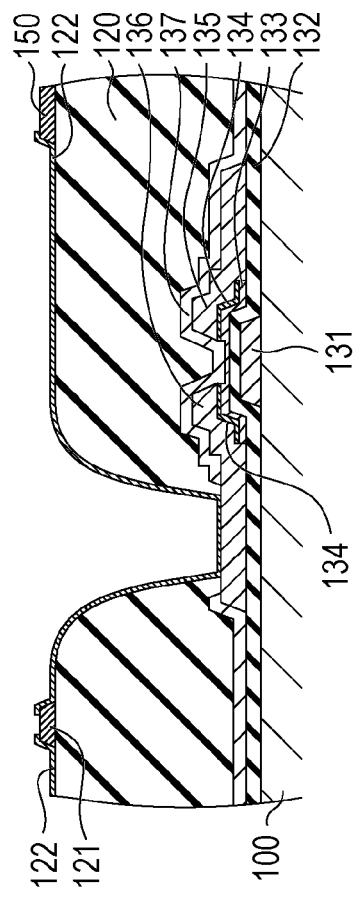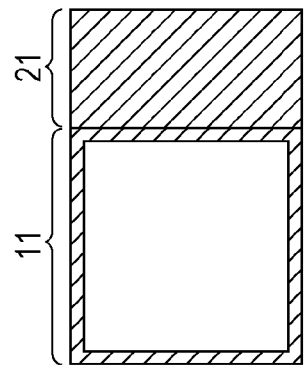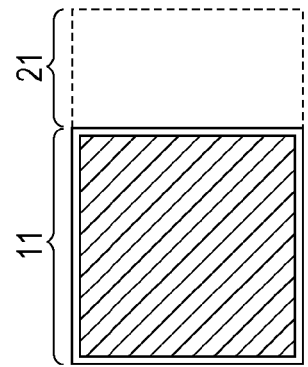

FIG. 11A
FIG. 11B
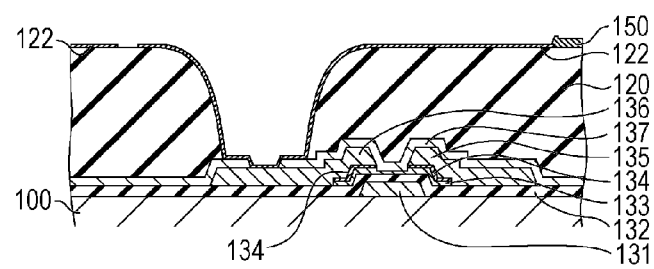
FIG. 11C
FIG. 11D
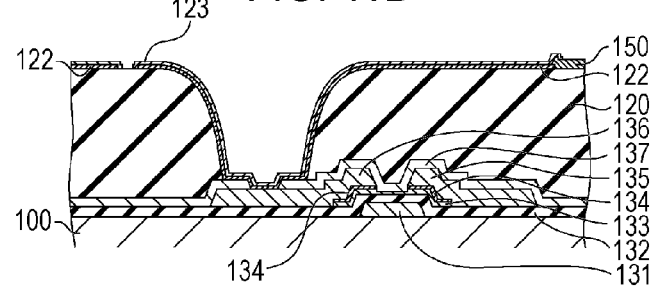
FIG. 11E
FIG. 11F
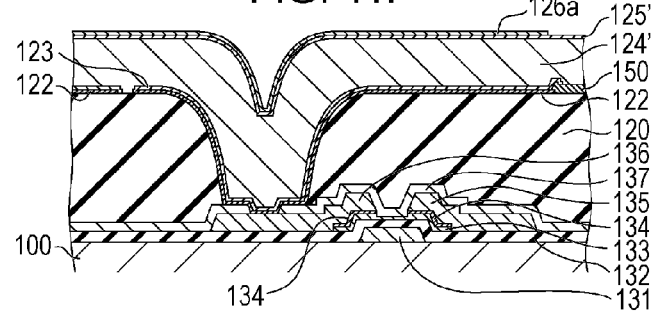
FIG. 11G
FIG. 11H
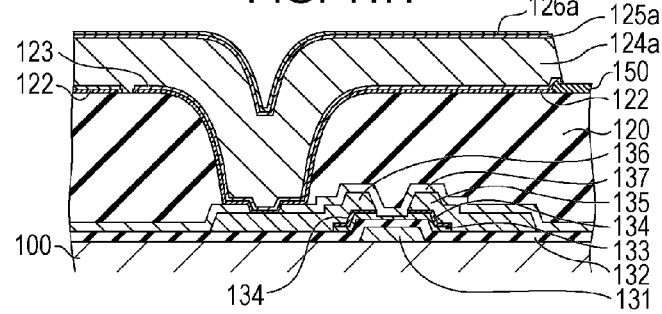

DETECTION APPARATUS HAVING INTERLAYER INSULATING LAYER COMPOSED OF ORGANIC MATERIAL AND COVERING LAYER COMPOSED OF INORGANIC MATERIAL, DETECTION SYSTEM, AND METHOD FOR PRODUCING DETECTION APPARATUS

BACKGROUND OF THE INVENTION

1. Field of the Invention

The present invention relates to a detection apparatus, a detection system, and a method for producing a detection apparatus that are applied to a medical image diagnostic apparatus, a nondestructive inspection apparatus, an analysis apparatus using radiation, or the like.

2. Description of the Related Art

In recent years, thin-film semiconductor production techniques have been applied to the fabrication of radiation detection apparatuses which include an array of pixels (a pixel array). In these apparatuses, each of the pixels is provided by combining a switching element, such as a thin film transistor (TFT), and a conversion element, such as a photodiode, that converts radiation or light into electric charge. A detection apparatus of the related art described in Japanese Patent Laid-Open No. 2007-035773 includes conversion elements provided on electrodes that are disposed on a substrate. The electrodes are composed of a transparent conductive oxide, and are separated from one another on a pixel-by-pixel basis. Furthermore, the detection apparatus of the related art further includes switching elements that are connected to the electrodes via contact holes provided in an interlayer insulating layer. The interlayer insulating layer is disposed between the substrate and the electrodes, and is composed of an organic material. The conversion elements of the detection apparatus of the related art are separated from one another on a pixel-by-pixel basis in such a manner that an impurity semiconductor layer and a semiconductor layer thereof are removed on the interlayer insulating layer. However, in the production of a structure described in Japanese Patent Laid-Open No. 2007-035773, in the case of depositing an impurity semiconductor film, which is to be the impurity semiconductor layer of the conversion elements, and a semiconductor film, which is to be the semiconductor layer of the conversion elements, and in the case of removing the impurity semiconductor film and the semiconductor film on the interlayer insulating layer, a process in which the interlayer insulating layer is exposed is present. More specifically, on the substrate, a region in which no pixel is disposed (a pixel-array outside region) is present outside a region in which multiple pixels are disposed (a pixel-array region). In order to make the thickness of the interlayer insulating layer uniform in the pixel-array region, the interlayer insulating layer is not only disposed within the pixel-array region, but also disposed so as to extend beyond the pixel-array region and reach the pixel-array outside region. Thus, in the case of forming the conversion elements, the exposed area of the interlayer insulating layer in the pixel-array outside region is larger than that of the interlayer insulating layer in the pixel-array region. When the interlayer insulating layer, which is composed of an organic material, is exposed in the case of forming the conversion elements using a chemical vapor deposition (CVD) method, an etching method, or the like, organic contamination in which the organic material is mixed into the conversion elements can occur. A large difference between the exposed areas of the interlayer insulating layer leads to a large difference between the degrees of organic contamination. Thus, there can be a large difference between the degree of organic contamination of the conversion elements located at the edges of the pixel-array region and the degree of organic contamination of the conversion elements located at the center of the pixel-array region. For this reason, the difference between the degrees of organic contamination leads to a large difference between the conversion characteristics of the conversion elements located at the edges of the pixel-array region and the conversion characteristics of the conversion elements located at the center of the pixel-array region. Therefore, the difference in conversion characteristics of the conversion elements located at the edges of the pixel-array region as compared to the conversion characteristics of the conversion elements located at the center of the pixel-array region can cause an image artifact to occur during imaging.

SUMMARY OF THE INVENTION

The present invention aims to solve such problems, and provides a detection apparatus in which mixing of an organic material from an interlayer insulating layer in an pixel-array outside region into an impurity semiconductor layer and a semiconductor layer of conversion elements is reduced, and in which, consequently, occurrence of an image artifact is reduced.

A detection apparatus according to the present invention includes a plurality of conversion elements, an interlayer insulating layer, and a covering layer. Each of the plurality of conversion elements includes an electrode electrically connected to a corresponding one of a plurality of switching elements and a semiconductor layer disposed on the electrode. The interlayer insulating layer is disposed so as to cover the plurality of switching elements and composed of an organic material, and has a surface including a first region and a second region located outside the first region. The electrodes are disposed on the surface of the interlayer insulating layer in the first region. The covering layer is disposed on the surface of the interlayer insulating layer in the second region and composed of an inorganic material.

Furthermore, a method for producing a detection apparatus according to the present invention is a method for producing a detection apparatus including a plurality of conversion elements. Each of the plurality of conversion elements includes an electrode electrically connected to a corresponding one of a plurality of switching elements, and a semiconductor layer disposed on the electrode. The method includes the following: a first step of forming an interlayer insulating layer so as to cover the plurality of switching elements, the interlayer insulating layer being composed of an organic material and having a surface including a first region and a second region located outside the first region, and forming the electrodes on the surface of the interlayer insulating layer in the first region and forming a covering layer on the surface of the interlayer insulating layer in the second region, the covering layer being composed of an inorganic material; and a second step of forming the semiconductor layer on the electrodes after the first step.

According to the present invention, a detection apparatus can be provided, in which mixing of an organic material from an interlayer insulating layer in an pixel-array outside region into an impurity semiconductor layer and a semiconductor layer of conversion elements is reduced, and in which, consequently, occurrence of an image artifact is reduced.

Further features of the present invention will become apparent from the following description of exemplary embodiments with reference to the attached drawings.

BRIEF DESCRIPTION OF THE DRAWINGS

FIGS. 8A and 8C are schematic plan views of mask patterns for explaining a method for producing the detection apparatus according to the third embodiment, and FIGS. 8B and 8D are schematic cross-sectional views for explaining the method for producing the detection apparatus according to the third embodiment.

FIGS. 11A, 11C, 11E, and 11G are schematic plan views of mask patterns for explaining a method for producing the detection apparatus according to the fourth embodiment, and FIGS. 11B, 11D, 11F, and 11H are schematic cross-sectional views for explaining the method for producing the detection apparatus according to the fourth embodiment.

DESCRIPTION OF THE EMBODIMENTS

Hereinafter, embodiments of the present invention will be specifically described with reference to the attached drawings. Note that, in the present specification, examples of radiation include not only alpha radiation, beta radiation, and gamma radiation that are beams constituted by particles (including photons) emitted by radioactive decay, but also beams having almost the same or more energy, such as X-rays, a particle beam, and cosmic rays.

First Embodiment

Figure 1A:
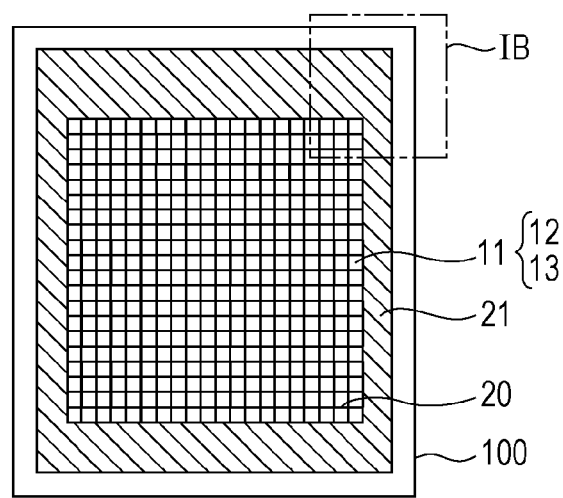
FIGS. 1A, 1B, and 1C are schematic plan views of a detection apparatus according to a first embodiment.
Figure 1B:
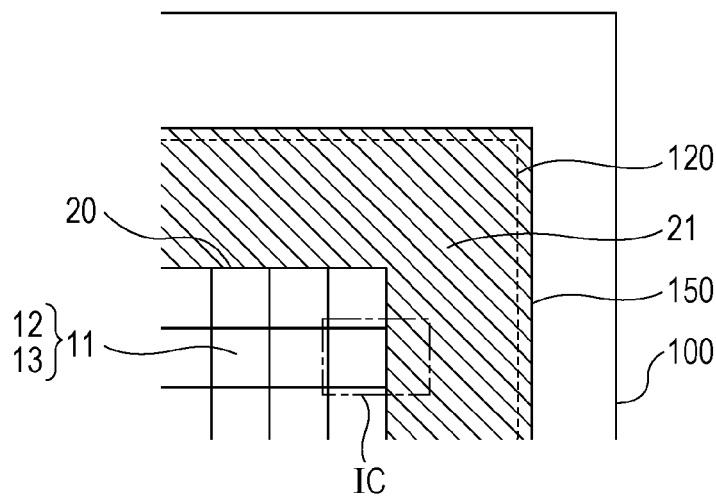
Figure 1C:
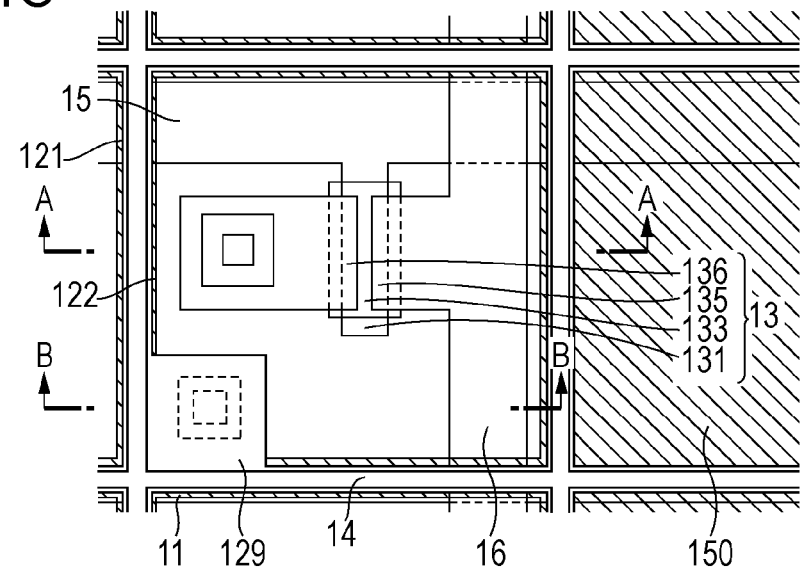

First, a planar structure of a detection apparatus according to a first embodiment of the present invention will be described using FIGS. 1A to 1C and FIGS. 2A to 2C. FIG. 1A is a schematic plan view of a substrate included in the detection apparatus, and FIG. 1B is a schematic plan view in which a region IB in FIG. 1A is enlarged. FIG. 1C is a plan view of each pixel in a region IC illustrated in FIG. 1B. Note that, in FIG. 1C, for simplicity, regarding a conversion element, only a first electrode is illustrated.

As illustrated in FIG. 1A, the detection apparatus according to the present invention includes multiple pixels 11 disposed on a substrate 100. On the substrate 100, a pixel-array region 20 that is a region in which the multiple pixels 11 are disposed is present. Furthermore, on the substrate 100, a pixel-array outside region 21 that is a region located outside the pixel-array region 20 is present. In the pixel-array outside region 21, multiple pixels are not disposed. As illustrated in FIG. 1C, each of the pixels 11 included in the detection apparatus according to the present invention includes a conversion element 12 that converts radiation or light into electric charge, and a TFT 13 that is a switching element which outputs an electric signal in accordance with the electric charge that the conversion element 12 has. A PIN photodiode is used as the conversion element 12. The TFTs 13 are provided on the insulating substrate 100 such as a glass substrate. Each of the conversion elements 12 is disposed in such a manner that the conversion element 12 and an interlayer insulating layer 120 composed of an organic material are stacked on a corresponding one of the TFTs 13 and the interlayer insulating layer 120 is sandwiched between the conversion element 12 and the TFT 13. The interlayer insulating layer 120 is disposed so as to cover the multiple TFTs 13 that are multiple switching elements. Note that, in the present embodiment, the surface of the substrate 100 has regions, and the interlayer insulating layer 120 is disposed so as to cover the surface of the substrate 100 in, among the regions, a region larger than a region in which the multiple TFTs 13 are disposed. Then, as illustrated in FIG. 1B, the surface of the interlayer insulating layer 120 has regions, and multiple first electrodes 122 are disposed on the surface of the interlayer insulating layer 120 in, among the regions, a first region that is located in the pixel-array region 20, and, consequently, the multiple pixels 11 including the multiple conversion elements 12 are disposed. In contrast, a covering layer 150 composed of an inorganic material is disposed on the surface of the interlayer insulating layer 120 in, among the regions, a second region that is provided outside the first region and that is located in the pixel-array outside region 21. Note that, in the present embodiment, the covering layer 150 composed of an inorganic material is disposed so as to cover the second region of the surface of the interlayer insulating layer 120. Note that the first electrodes 122 correspond to electrodes of conversion elements of the present invention.

Figure 2A:
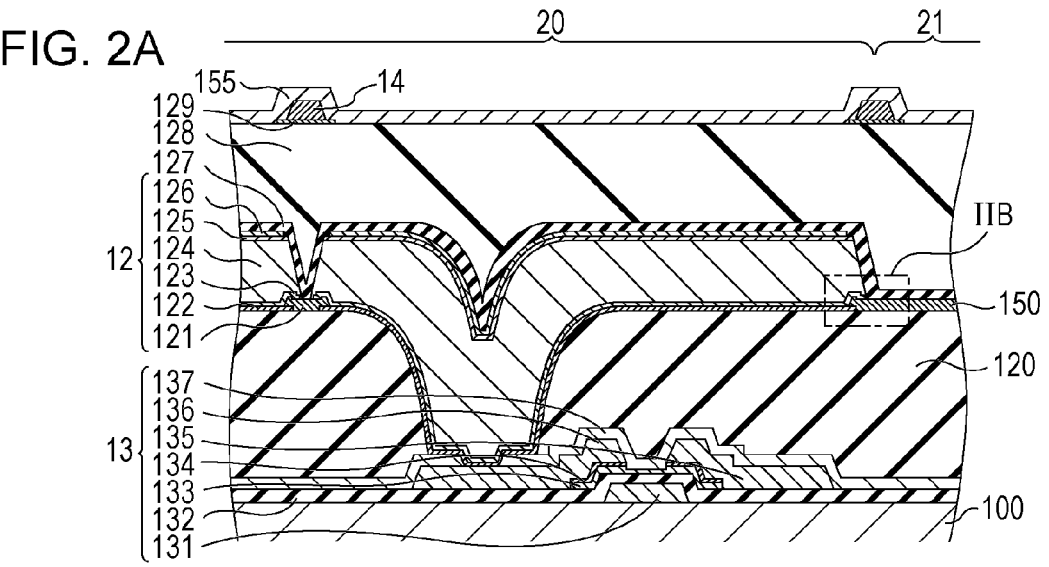
FIGS. 2A, 2B, and 2C are schematic cross-sectional views of the detection apparatus according to the first embodiment.
Figure 2B:
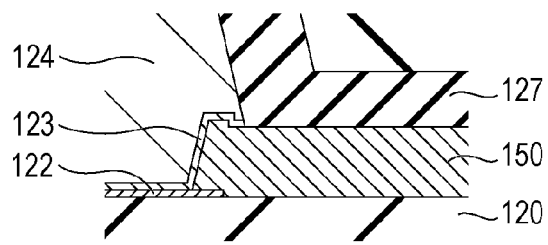
Figure 2C:
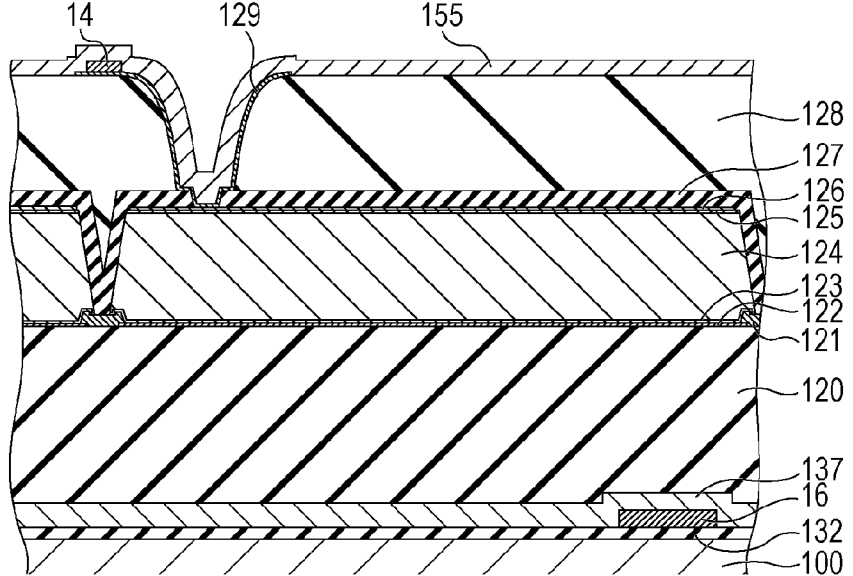

Next, a cross-sectional structure of the detection apparatus according to the first embodiment of the present invention will be described with reference to FIG. 1C and FIGS. 2A to 2C. FIG. 2A is a schematic cross-sectional view taken along the line A-A in FIG. 1C, FIG. 2B is a schematic cross-sectional view in which a region IIB in FIG. 2A is enlarged, and FIG. 2C is a schematic cross-sectional view taken along the line B-B in FIG. 1C. Note that, in FIGS. 2A to 2C, individual insulating layers and individual layers included in the conversion elements 12 that are not illustrated in FIG. 1C are also illustrated.

Each of the TFTs 13 includes a control electrode 131, an insulating layer 132, a semiconductor layer 133, an impurity semiconductor layer 134 having an impurity concentration higher than that of the semiconductor layer 133, a first main electrode 135, and a second main electrode 136 that are provided on the substrate 100 in this order from the substrate side. Certain regions of the impurity semiconductor layer 134 are in contact with the first main electrode 135 and the second main electrode 136, and a region of the semiconductor layer 133 between regions of the semiconductor layer 133 that are regions in contact with the certain regions is a channel region of the TFT 13. The control electrode 131 is electrically connected to a corresponding one of control wiring patterns 15. The first main electrode 135 is electrically connected to a corresponding one of signal wiring patterns 16. The second main electrode 136 is electrically connected to the first electrode 122 of a corresponding one of the conversion elements 12. Note that, in the present embodiment, the first main electrodes 135, the second main electrodes 136, and the signal wiring patterns 16 are formed together in the same conductive layer, and the first main electrodes 135 are formed as portions of the signal wiring patterns 16. A protective layer 137 is provided so as to cover the TFTs 13, the control wiring patterns 15, and the signal wiring patterns 16. In the present embodiment, although an inversely-staggered TFT using the semiconductor layer 133 and the impurity semiconductor layer 134 that are composed mainly of amorphous silicon is used as each switching element, the present invention is not limited thereto. For example, a staggered TFT that is composed mainly of polycrystalline silicon can be used, or an organic TFT, an oxide TFT, or the like can be used.

The interlayer insulating layer 120 is disposed between the substrate 100 and the multiple first electrodes 122, which are described below, so as to cover the multiple TFTs 13, and has contact holes. The first electrode 122 of each of the conversion elements 12 and the second main electrode 136 of a corresponding one of the TFTs 13 are electrically connected to each other in a corresponding one of the contact holes provided in the interlayer insulating layer 120.

Each of the conversion elements 12 includes a corresponding one of the first electrodes 122, a first-conductivity-type impurity semiconductor layer 123, a semiconductor layer 124, a second-conductivity-type impurity semiconductor layer 125, and a second electrode 126 that are provided on the interlayer insulating layer 120 in this order from the interlayer insulating layer side. Here, the first-conductivity-type impurity semiconductor layer 123 has a first-conductivity-type polarity, and has a first-conductivity-type impurity concentration higher than that of each of the semiconductor layer 124 and the second-conductivity-type impurity semiconductor layer 125. Furthermore, the second-conductivity-type impurity semiconductor layer 125 has a second-conductivity-type polarity, and has a second-conductivity-type impurity concentration higher than that of each of the first-conductivity-type impurity semiconductor layer 123 and the semiconductor layer 124. The first conductivity type and the second conductivity type are conductivity types having polarities different from each other. For example, when the first conductivity type is n type, the second conductivity type is p type. A corresponding one of the electrode wiring patterns 14 is electrically connected to the second electrode 126 of the conversion element 12. The first electrode 122 of the conversion element 12 is electrically connected to the second main electrode 136 of a corresponding one of the TFTs 13 in a corresponding one of the contact holes provided in the interlayer insulating layer 120. Note that, although a photodiode using the first-conductivity-type impurity semiconductor layer 123, the semiconductor layer 124, and the second-conductivity-type impurity semiconductor layer 125 that are composed mainly of amorphous silicon is used in the present embodiment, the present invention is not limited thereto. For example, an element that uses a first-conductivity-type impurity semiconductor layer 123, a semiconductor layer 124, and a second-conductivity-type impurity semiconductor layer 125 which are composed mainly of amorphous selenium and that converts radiation directly into electric charge can be used. Note that the second electrodes 126 correspond to other electrodes of the conversion elements of the present invention.

As illustrated in FIGS. 2A to 2C, the multiple first electrodes 122 are disposed on the surface of the interlayer insulating layer 120 in the first region that is located in the pixel-array region 20, and, consequently, the multiple pixels 11 including the multiple conversion elements 12 are disposed. In contrast, the covering layer 150 composed of an inorganic material is disposed, so as to be in contact with the interlayer insulating layer 120, on the surface of the interlayer insulating layer 120 in the second region that is provided outside the first region and that is located in the pixel-array outside region 21. Note that, in the present embodiment, covering members 121 composed of an inorganic material are disposed, so as to be in contact with the interlayer insulating layer 120, between the multiple first electrodes 122 on the surface of the interlayer insulating layer 120 in the first region that is located in the pixel-array region 20. The first electrodes 122, the covering members 121, and the covering layer 150 are disposed on the interlayer insulating layer 120 so as to cover the surface of the interlayer insulating layer 120. Thus, in the case of depositing an impurity semiconductor film, which is to be the impurity semiconductor layer 123, using a CVD method, an evaporation method, a sputtering method, or the like, exposure of the surface of the interlayer insulating layer 120 is reduced. Therefore, mixing of the organic material into the impurity semiconductor layer of the conversion elements 12 included in the pixels 11 located at the edges of the pixel-array region 20 can be reduced. Thus, occurrence of an image artifact due to the differences between the outputs of the pixels 11 that are located at the center of the pixel-array region 20 and the outputs of the pixels 11 that are located at the edges of the pixel-array region 20 can be reduced. Furthermore, in the present embodiment, the impurity semiconductor layer 123, the semiconductor layer 124, and the impurity semiconductor layer 125 are separated into pieces on a pixel-by-pixel basis on the covering members 121. Moreover, in the pixel-array outside region 21, the impurity semiconductor layer 123, the semiconductor layer 124, and the impurity semiconductor layer 125 are removed by dry etching or the like. In the separation and the removal, the covering members 121 and the covering layer 150 serve as an etching stopper layer. Therefore, the interlayer insulating layer 120 is not exposed to etch species used in dry etching, and, consequently, contamination of the individual layers of the conversion elements 12 with the organic material can be reduced.

Additionally, an insulating layer 127 and an interlayer insulating layer 128 are disposed so as to cover the conversion elements 12. The second electrode 126 of each of the conversion elements 12 and a corresponding one of the electrode wiring patterns 14 are electrically connected to each other via a conductive layer 129 in a corresponding one of contact holes provided in the insulating layer 127 and the interlayer insulating layer 128. In addition, a passivation layer 155 is provided so as to cover the electrode wiring patterns 14, the conductive layer 129, and the interlayer insulating layer 128.

Next, a method for producing the detection apparatus according to the first embodiment of the present invention will be described using FIGS. 3A to 3J and FIGS. 4A to 4H. Particularly, a process of forming contact holes in the interlayer insulating layer 120 and processes thereafter will be described in detail using mask patterns and cross-sectional views of the detection apparatus that is being subjected to the processes. Note that each of FIGS. 3A, 3C, 3E, 3G, 3I, 4A, 4C, 4E, and 4G is a schematic plan view of a mask pattern of a photomask used in a corresponding one of the processes. Furthermore, each of FIGS. 3B, 3D, 3F, 3H, 3J, 4B, 4D, 4F, and 4H is a schematic cross-sectional view taken along the line A-A in FIG. 1C in a corresponding one of the processes.

First, the multiple TFTs 13 are provided on the insulating substrate 100, and the protective film 137 is provided so as to cover the multiple TFTs 13. Portions of the protective film 137 that are portions located on the second main electrodes 136 and that are to be electrically connected to the photodiodes are subjected to etching, thereby providing contact holes in the protective film 137. Then, in the process illustrated in FIG. 3B, using a coating apparatus such as a spinner, a film composed of an acrylic resin that is an organic material having a photosensitivity is deposited as an interlayer insulating film so as to cover the TFTs 13 and the protective film 137. Alternatively, a polyimide resin or the like can be used as the organic material having a photosensitivity. Then, a light exposure process and a development process are performed using the mask illustrated in FIG. 3A, thereby forming the interlayer insulating layer 120 having contact holes.

Figure 3A:
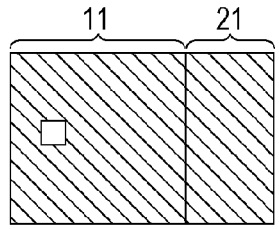
FIGS. 3A, 3C, 3E, 3G, and 3I are schematic plan views of mask patterns for explaining a method for producing the detection apparatus according to the first embodiment.
Figure 3B:
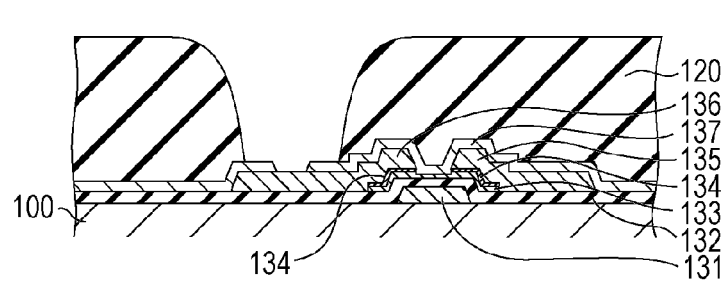
FIGS. 3B, 3D, 3F, 3H, and 3J are schematic cross-sectional views of the detection apparatus for explaining the method for producing the detection apparatus according to the first embodiment.
Figure 3C:
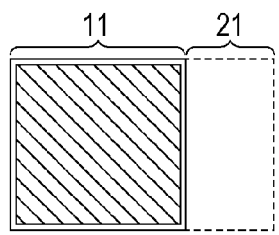
Figure 3D:
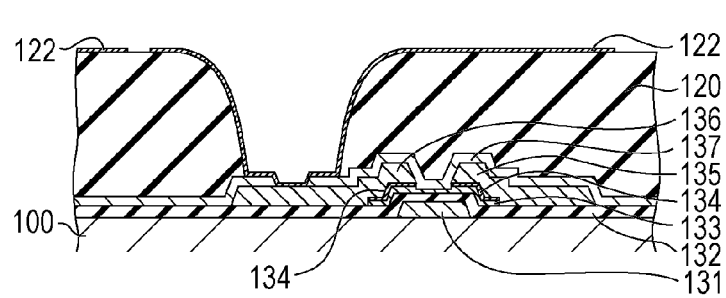
Figure 3E:
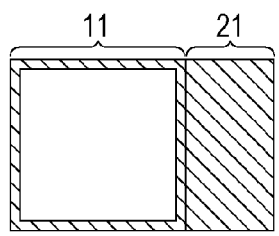

Next, in the process illustrated in FIG. 3D, a conductive film is deposited so as to cover the interlayer insulating layer 120. Then, the conductive film is subjected to etching using the mask illustrated in FIG. 3C, thereby forming the first electrodes 122 of the conversion elements 12. Note that, in the present embodiment, a transparent conductive oxide film that is composed of ITO and that is an amorphous film is used as the conductive film. The transparent conductive oxide film is subjected to wet etching using the mask illustrated in FIG. 3E, and subjected to an annealing process so as to be changed to a polycrystalline film, thereby forming the first electrodes 122 of the conversion elements 12. However, a film composed of a metallic material may be used as the conductive film.

Figure 3F:
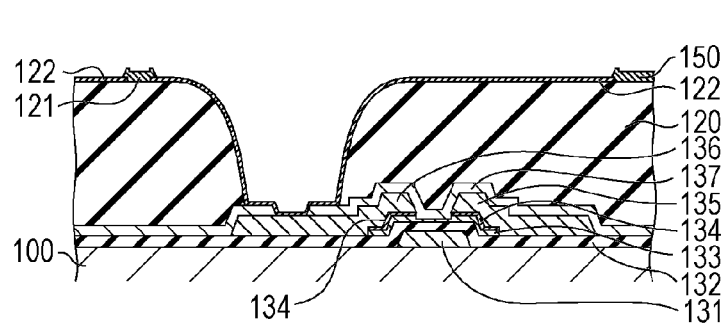
Figure 3G:
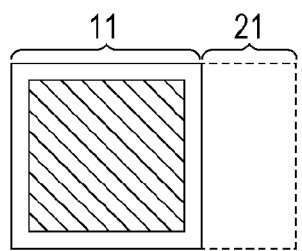

Next, in the process illustrated in FIG. 3F, an insulating film that is composed of a typical inorganic material, such as a silicon nitride film or a silicon oxide film, is deposited using a plasma CVD method so as to cover the interlayer insulating layer 120. Then, the insulating film is subjected to etching using the mask illustrated in FIG. 3E, whereby the covering members 121 and the covering layer 150 are formed between the multiple first electrodes 122 on the surface of the interlayer insulating layer 120 in the first region and on the surface of the interlayer insulating layer 120 in the second region, respectively. Accordingly, the surface of the interlayer insulating layer 120 is covered with the multiple covering members 121, the multiple first electrodes 122, and the covering layer 150. In the present embodiment, the process illustrated in FIG. 3D and the process illustrated in FIG. 3F correspond to a first step of the present invention. Note that, in the present embodiment, an example is described, in which an inorganic insulating material that is the same as the material that the covering members 121 are composed of is used as the material that the covering layer 150 is composed of, and in which the covering layer 150 and the covering members 121 are formed together. However, the present invention is not limited thereto. For example, the covering members 121 and the covering layer 150 may be formed in different processes. Furthermore, the material that the covering layer 150 is composed of is not limited to an inorganic insulating material, and any inorganic film that can cover the surface of the interlayer insulating layer 120 may be used. For example, among regions of the covering layer 150, regions that are in contact with the first electrodes 122 and the impurity semiconductor layer 123 may be formed of an inorganic insulating material, and the other regions may be formed of an inorganic conductive material, such as ITO, Al, or Cu.

Figure 3H:
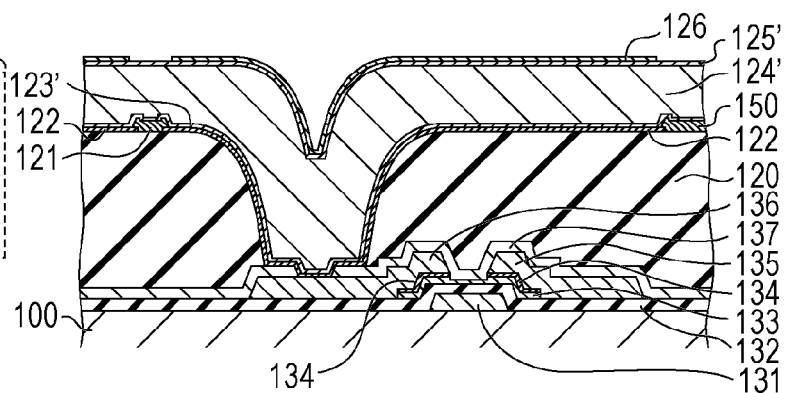

Next, in the process illustrated in FIG. 3H, an amorphous silicon film in which a pentavalent element, such as phosphorus, is implanted as an impurity is deposited as a first-conductivity-type impurity semiconductor film 123' using a plasma CVD method so as to cover the covering members 121 and the first electrodes 122. Next, a semiconductor film 124' that is an amorphous silicon film and an amorphous silicon film, as a second-conductivity-type impurity semiconductor film 125', in which a trivalent element, such as boron, is implanted as an impurity are deposited in this order using a plasma CVD method or the like. In the case of depositing the impurity semiconductor film 123', when the interlayer insulating layer 120 is not covered with the covering members 121, the covering layer 150, and the first electrodes 122, the interlayer insulating layer 120 is exposed to plasma. When the interlayer insulating layer 120 composed of an organic material is exposed to plasma, the organic material spatters, and mixes into the impurity semiconductor film 123'. Thus, junctions between the first electrodes 122 and the impurity semiconductor layer 123 are contaminated in some cases. Particularly, the exposed area of the interlayer insulating layer 120 in the pixel-array outside region 21 is larger than the exposed area of the interlayer insulating layer 120 in the pixel-array region 20. Thus, the degree of organic contamination of the conversion elements 12 included in the pixels 11 located at the edges of the pixel-array region 20 is higher than that of organic contamination of the conversion elements 12 included in the pixels 11 located at the center of the pixel-array region 20. For this reason, in the present embodiment, a structure is used, in which the surface of the interlayer insulating layer 120 in the pixel-array region 20 is covered with the covering members 121, the first electrodes 122, and the covering layer 150, and, in which, consequently, the surface of the interlayer insulating layer 120 is not exposed in the case of depositing the impurity semiconductor film 123' that is to be the first-conductivity-type impurity semiconductor layer 123. Accordingly, in the case of depositing the impurity semiconductor film 123' that is to be the impurity semiconductor layer 123, mixing of the organic material into the impurity semiconductor film 123' due to scattering of the organic material can be reduced. Thus, occurrence of an image artifact can be reduced. Next, a transparent conductive oxide film is deposited using a sputtering method so as to cover an impurity semiconductor film 125'. Next, the transparent conductive oxide film is subjected to wet etching using the mask illustrated in FIG. 3G, thereby forming the second electrodes 126 of the conversion elements 12. Note that, in the present embodiment, a transparent conductive oxide is used as the material that the second electrodes 126 are composed of. However, the present invention is not limited thereto. Any conductive film may be used. For example, in the case where an element that converts radiation directly into electric charge is used as each of the conversion elements 12, a conductive film that radiation easily passes through, such as an Al film, can be used.

Figure 3I:
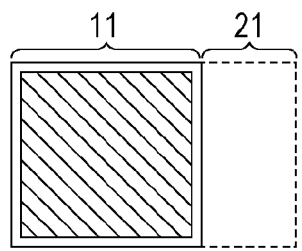
Figure 3J:
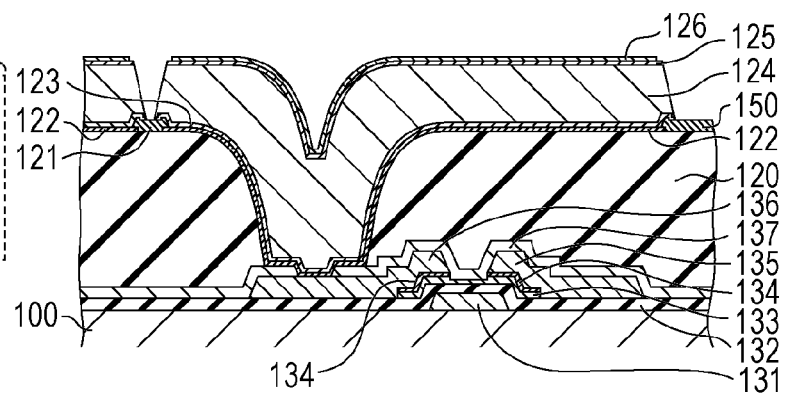

Next, in the process illustrated in FIG. 3J, the impurity semiconductor film 125', the semiconductor film 124', and the impurity semiconductor film 123' are removed by dry etching using the mask illustrated in FIG. 3I. Accordingly, the conversion elements 12 are separated from one another on a pixel-by-pixel basis, and the impurity semiconductor film 125', the semiconductor film 124', and the impurity semiconductor film 123' in the pixel-array outside region 21 are removed. In the conversion elements 12 that have been separated from one another, the impurity semiconductor layer 125, the semiconductor layer 124, and the impurity semiconductor layer 123 are formed.

Figure 4A:
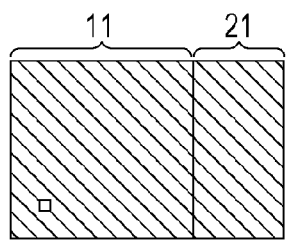
FIGS. 4A, 4C, 4E, and 4G are schematic plan views of mask patterns for explaining the method for producing the detection apparatus according to the first embodiment.
Figure 4B:
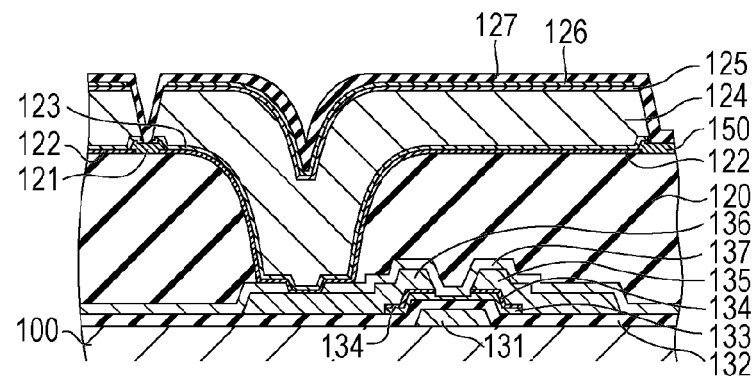
FIGS. 4B, 4D, 4F, and 4H are schematic cross-sectional views the detection apparatus for explaining the method for producing the detection apparatus according to the first embodiment.
Figure 4C:
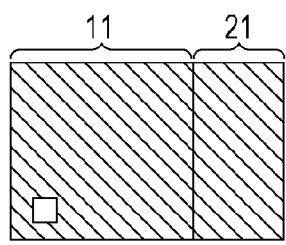

Next, in the process illustrated in FIG. 4B, an insulating film composed of an inorganic material, such as a silicon nitride film, is deposited using a plasma CVD method so as to cover the conversion elements 12 and the covering members 121. Also in the case of depositing this insulating film, a structure in which exposure of the interlayer insulating layer 120 is reduced by the covering layer 150 is used. Thus, contamination of the individual layers with the organic material can be reduced. Then, the insulating film is subjected to dry etching using the mask illustrated in FIG. 4A, thereby forming the insulating layer 127 having contact holes.

Figure 4D:
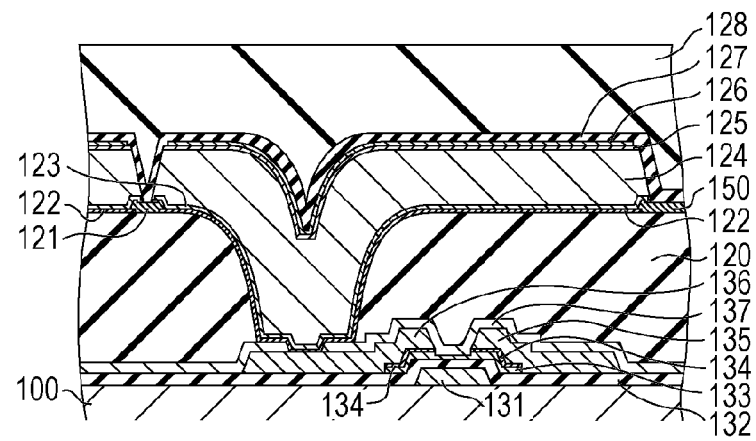
Figure 4E:
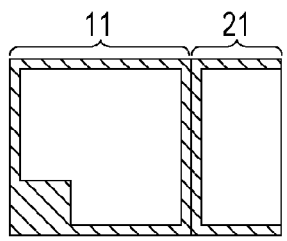

Next, in the process illustrated in FIG. 4D, a layer composed of an acrylic resin that is an organic material having a photosensitivity is deposited as an interlayer insulating layer so as to cover the second electrodes 126 and the insulating layer 127. Then, the interlayer insulating layer 128 having contact holes is formed using the mask illustrated in FIG. 4C.

Figure 4F:
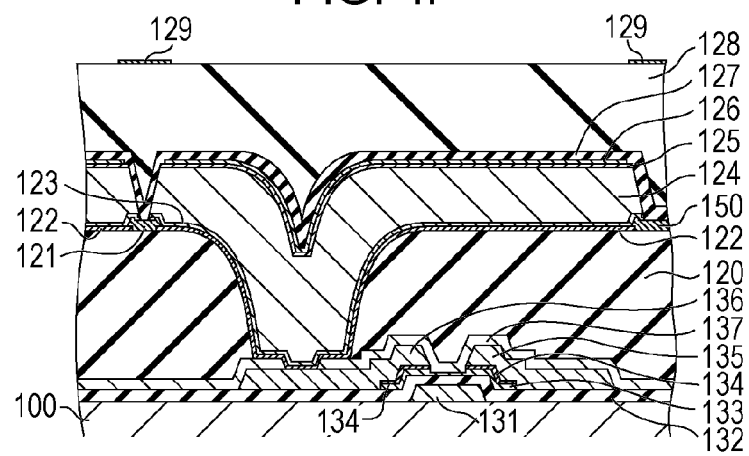
Figure 4G:
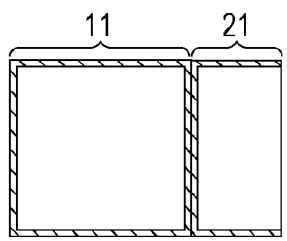

Next, in the process illustrated in FIG. 4F, a transparent conductive oxide film is deposited using a sputtering method. Next, the transparent conductive oxide film is subjected to wet etching using the mask illustrated in FIG. 4E, thereby forming the conductive layer 129.

Figure 4H:
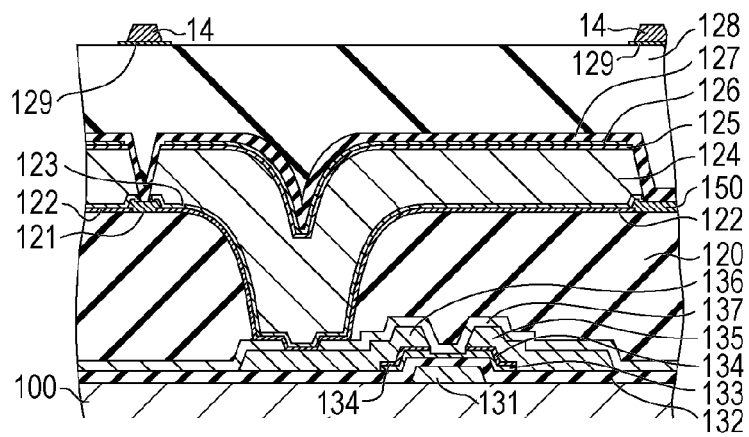

Next, in the process illustrated in FIG. 4H, a conductive film, such as an Al film, that is to be the electrode wiring patterns 14 is deposited using a sputtering method. Then, the conductive film is subjected to wet etching using the mask illustrated in FIG. 4G, thereby forming the electrode wiring patterns 14. By performing this process, the electrode wiring patterns 14 and the second electrodes 126 of the conversion elements 12 are electrically connected to each other with the conductive layer 129. In this case, because the conductive layer 129 is formed of a transparent conductive oxide, a reduction in the aperture ratio can be prevented.

Then, the passivation layer 155 is formed so as to cover the electrode wiring patterns 14, the conductive layer 129, and the interlayer insulating layer 128, thereby obtaining the structure illustrated in FIG. 2A. Also in the case of forming the passivation layer 155, a structure is used, in which the interlayer insulating layer 120 is not exposed in the outside of the area in which the pixels are disposed. Thus, contamination of the individual layers with the organic material can be reduced. In the present embodiment, the process illustrated in FIG. 3H and the processes thereafter correspond to a second step of the present invention.

Figure 5:
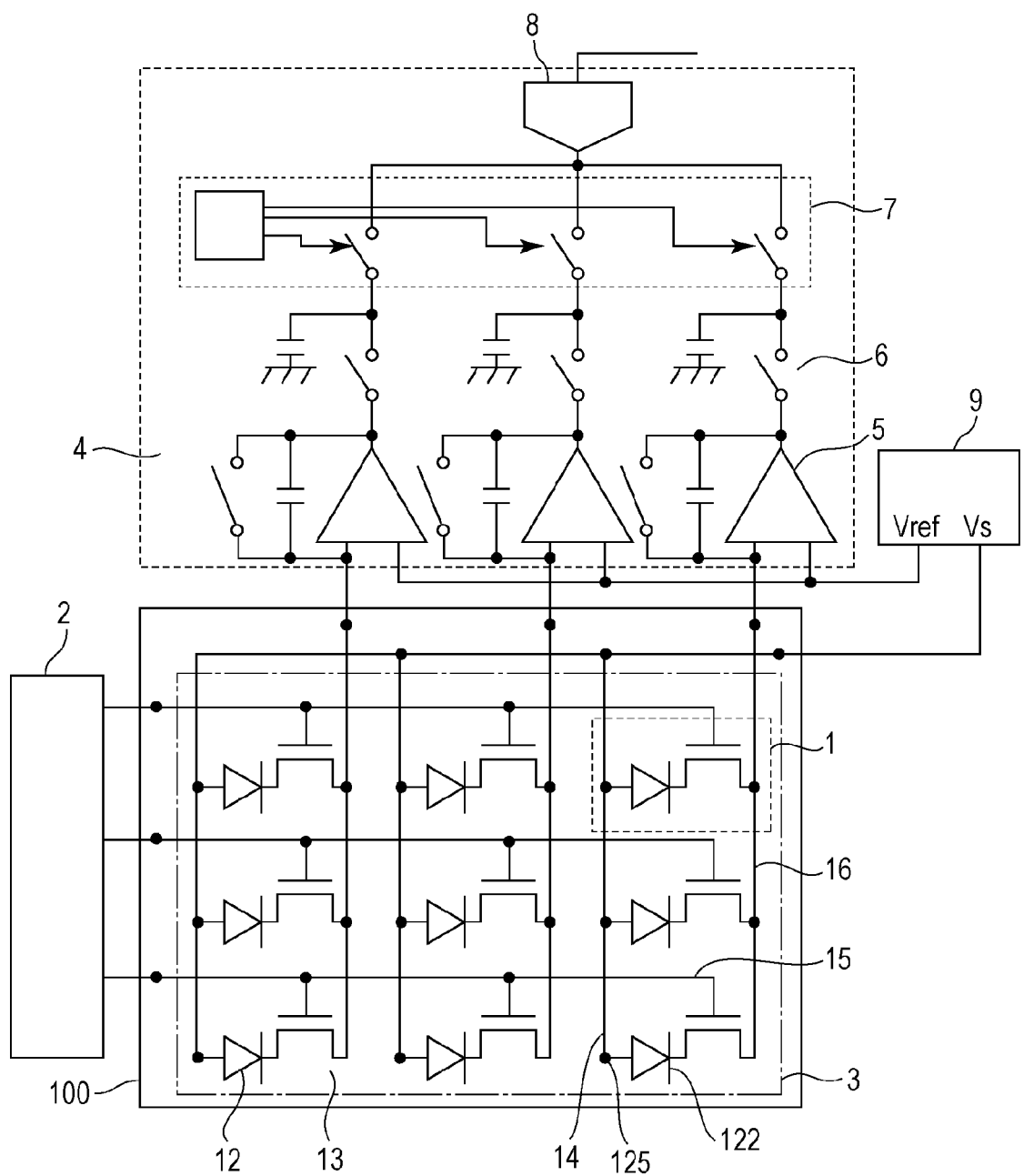
FIG. 5 is a diagram of an equivalent circuit of the detection apparatus according to the first embodiment of the present invention.

Next, a schematic equivalent circuit of the detection apparatus according to the first embodiment of the present invention will be described using FIG. 5. Note that, in FIG. 5, for simplicity of description, a diagram of an equivalent circuit in three rows and three columns is used. However, the present invention is not limited thereto. The detection apparatus has a pixel array in n rows and m columns (where each of n and m is a natural number equal to or larger than two). Regarding the detection apparatus according to the present embodiment, a conversion unit 3 including multiple pixels 1 that are arranged along the row direction and the column direction is provided on the surface of the substrate 100. Each of the pixels 1 includes a corresponding one of the conversion elements 12, which convert radiation or light into electric charge, and a corresponding one of the TFTs 13, which output electric signals in accordance with the electric charge that the conversion elements 12 have. A scintillator (not illustrated) that performs wavelength conversion so that radiation will be converted into visible light may be disposed on the surface of the conversion elements 12 on the second electrode 126 side.

The electrode wiring patterns 14 are connected to the second electrodes 126 of the conversion elements 12 as a wiring pattern common to the conversion elements 12. The control wiring patterns 15 are connected to the control electrodes 131 of the multiple TFTs 13, as wiring patterns common to the TFTs 13 arranged along the row direction, and are electrically connected to a driving circuit 2. The driving circuit 2 sequentially or simultaneously supplies driving pulses to the multiple control wiring patterns 15, which are arranged along the column direction, whereby electric signals are output, in parallel, from the pixels 1 on a row-by-row basis to the multiple signal wiring patterns 16, which are arranged along the row direction. The signal wiring patterns 16 are connected to the first main electrodes 135 of the multiple TFTs 13, as wiring patterns common to the TFTs 13 arranged along the column direction, and are electrically connected to a reading circuit 4. The reading circuit 4 includes, for each of the signal wiring patterns 16, an integrating amplifier 5 that integrates and amplifies the electric signal output from the signal wiring pattern 16, and a sample and hold circuit 6 that samples and holds the electric signal which has been amplified and output by the integrating amplifier 5. The reading circuit 4 further includes a multiplexer 7 that converts the electric signals output in parallel from the multiple sample and hold circuits 6 into an electric signal in series, and an A/D converter 8 that converts the output electric signal into digital data. A reference potential Vref is supplied from a power supply circuit 9 to the non-inverting input terminals of the integrating amplifiers 5. Furthermore, the power supply circuit 9 is electrically connected to the multiple electrode wiring patterns 14 that are arranged along the row direction, and supplies a bias potential Vs to the second electrodes 126 of the conversion elements 12.

Hereinafter, an operation of the detection apparatus according to the present embodiment will be described. The reference potential Vref is supplied via the TFTs 13 to the first electrodes 122 of the conversion elements 12. The bias potential Vs that is necessary to perform electron-hole pair separation for electric charge generated from radiation or visible light is supplied to the second electrodes 126. In this state, radiation that passes through a subject or visible light based on the radiation enters the conversion elements 12, and is converted into electric charge. The electric charge is accumulated in the conversion elements 12. The driving pulses applied to the control wiring patterns 15 from the driving circuit 2 cause the TFTs 13 to enter a conduction state, whereby electric signals based on the electric charge are output to the signal wiring patterns 16. The electric signals are read to the outside as digital data by the reading circuit 4.

Second Embodiment

Next, a structure of each pixel included in a detection apparatus according to a second embodiment of the present invention will be described using FIGS. 6A to 6D. Each of FIGS. 6A to 6D is a schematic cross-sectional view taken along the line A-A in FIG. 1C.

The difference of the present embodiment from the first embodiment is the following. In other words, in each of the contact holes in which the conversion elements 12 and the TFTs 13 are connected to each other, a protective member 160 for protecting the second main electrode 136 and the protective film 137 is disposed in accordance with the stepped portion of the protective film 137 and the stepped portion of the interlayer insulating layer 120.

In the process illustrated in FIG. 3F, in the case of etching performed in order to form the covering members 121 and the covering layer 150, the second main electrodes 136 and the protective film 137 need to be protected by the first electrodes 122. However, protection of the second main electrodes 136 and the protective film 137 is impossible in some cases because of the crystallizability or thickness of the first electrodes 122. More specifically, in each of the contact holes of the interlayer insulating layer 120, when a conductive film that is to be the first electrode 122 is deposited on the stepped portion of the protective film 137 or the stepped portion of the interlayer insulating layer 120, the crystallizability of the first electrode 122 on the stepped portion decreases. The first electrode 122 on the stepped portion is easily subjected to etching. Thus, in the case of forming the covering members 121 and the covering layer 150, protection of the second main electrodes 136 and the protective film 137 with the first electrodes 122 is impossible, and, consequently, the second main electrode 136 and the insulating layer 127 are undesirably subjected to etching.

Thus, in the structure in the present embodiment, in each of the contact holes of the interlayer insulating layer 120, the protective member 160 for protecting the second main electrode 136 and the protective film 137 is disposed in accordance with the stepped portion of the protective film 137 and the stepped portion of the interlayer insulating layer 120. Therefore, in the process illustrated in FIG. 3F, the second main electrodes 136 and the protective film 137 are prevented from being undesirably subjected to etching, and, consequently, the second main electrodes 136 and the protective film 137 can be protected.

Figure 6A:
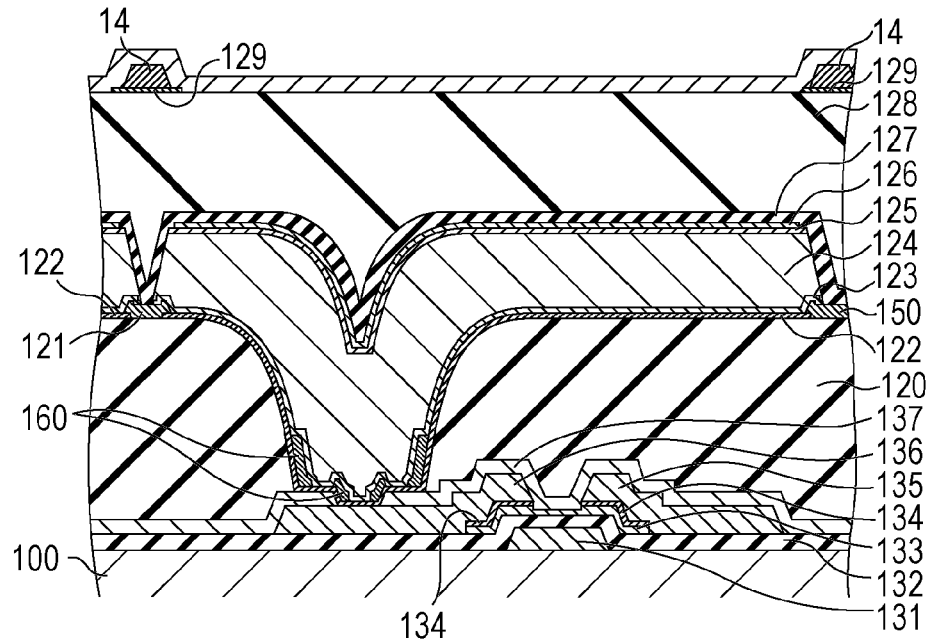
FIGS. 6A to 6D are schematic cross-sectional views of a detection apparatus according to a second embodiment.

In a structure illustrated in FIG. 6A, in each of the contact holes of the interlayer insulating layer 120, the protective member 160 is disposed so as to cover the stepped portion of the protective film 137 and the stepped portion of the interlayer insulating layer 120. A method for producing the structure illustrated in FIG. 6A will be described below. In the present embodiment, in the process illustrated in FIG. 3F in the first embodiment, the covering members 121 and the covering layer 150 are formed, and, simultaneously, the protective members 160 are formed from the same material, thereby obtaining the structure illustrated in FIG. 6A. Note that, in FIG. 6A, a structure is illustrated, in which each of the protective members 160 covers only the stepped portion of the protective film 137 and the stepped portion of the interlayer insulating layer 120. However, the present invention is not limited thereto.

Figure 6B:
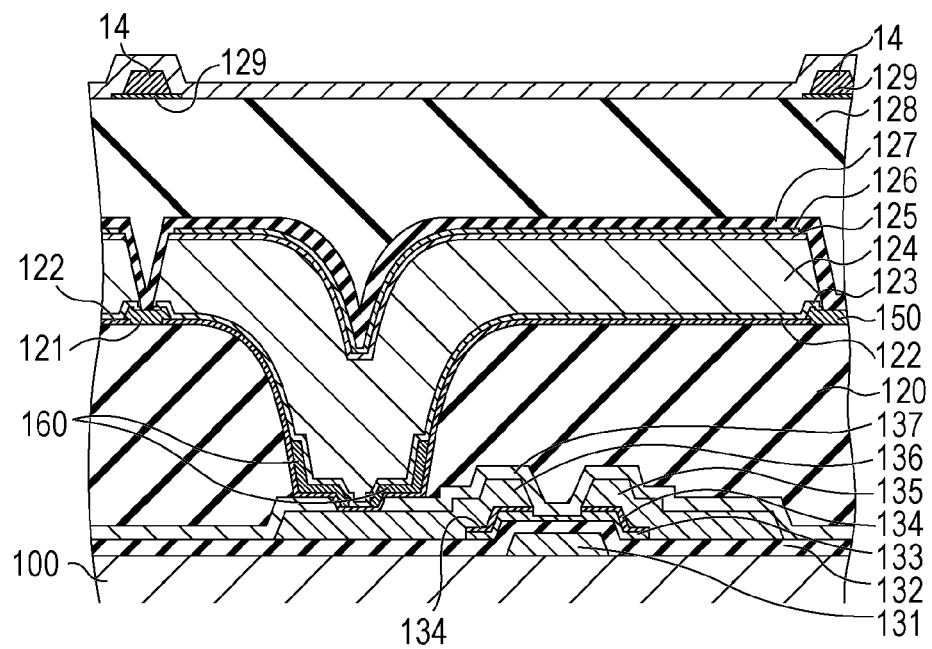

For example, as illustrated in FIG. 6B, a structure may be used, in which each of the protective members 160 is disposed so as to also cover the surface of the protective film 137 located in the bottom surface of a corresponding one of the contact holes, in addition to the stepped portion of the protective film 137 and the stepped portion of the interlayer insulating layer 120. With this structure, the protective film 137 can be more assuredly protected, compared with that with the structure illustrated in FIG. 6A.

Figure 6C:
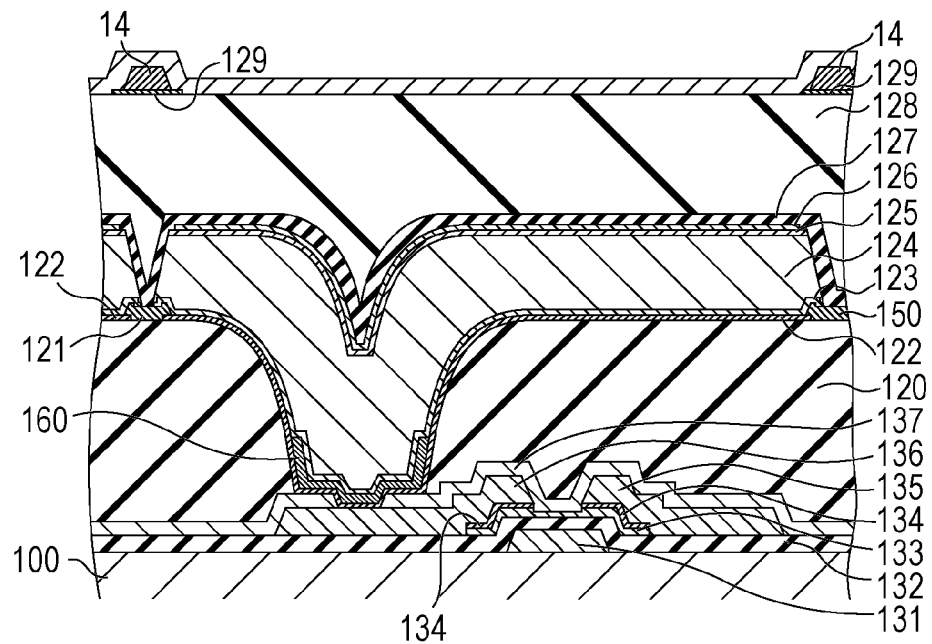

Furthermore, as illustrated in FIG. 6C, a structure may be used, in which each of the protective members 160 is disposed so as to cover the entire bottom surface of a corresponding one of the contact holes of the interlayer insulating layer 120. With this structure, the second main electrodes 136 can be more assuredly protected, compared with that with the structure illustrated in FIG. 6B.

Note that, regarding the protective members 160 illustrated in FIGS. 6A to 6C, when each of the protective members 160 is formed so as to also cover the surface of the first electrode 122 located outside a corresponding one of the contact holes of the interlayer insulating layer 120, the protective member 160 can cover the entire stepped portion of the first electrode 122 that is stepped because of the contact hole. Even when the protective members 160 are formed from an inorganic insulating layer and, consequently, the area of each of the protective members 160 increases, the impurity semiconductor layer 123 is disposed on the entire surface of the protective member 160. Thus, electric charge can be collected without any problem.

Figure 6D:
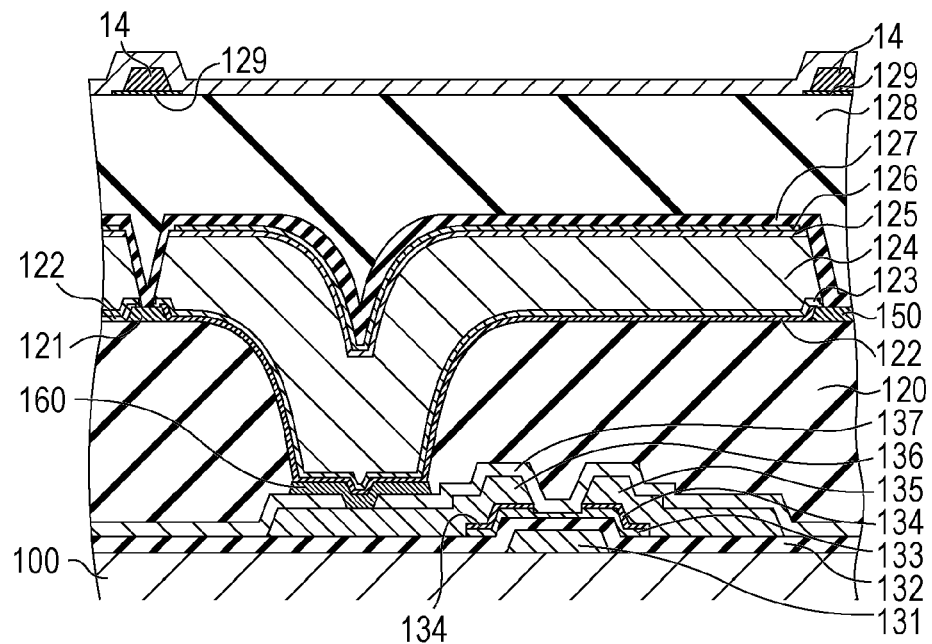

Note that, with reference to FIGS. 6A to 6C, a method is described, in which the protective members 160 are formed simultaneously with formation of the covering members 121 and the covering layer 150. However, the present invention is not limited thereto. Before the process illustrated in FIG. 3F is performed, the protective members 160 may be formed in advance. In this case, a material that has a conductivity and that has a resistance to etching which is to be performed for the covering members 121 and the covering layer 150 needs to be used as the material that the protective members 160 are composed of. For example, in the case where the covering members 121 and the covering layer 150 are to be composed of silicon nitride and where the covering members 121 and the covering layer 150 are to be formed by wet etching using hydrofluoric acid or the like, the material that the protective members 160 are composed of may be any one of the following materials. Examples of the material that the protective members 160 are composed of include metallic materials such as Mo, Cr, Pt, and Au, an alloy material such as MoCr, and semiconductor materials such as titanium oxide and titanium nitride that have resistance to hydrofluoric acid. Alternatively, in the case where the covering members 121 and the covering layer 150 are to be composed of silicon nitride and where the covering members 121 and the covering layer 150 are to be formed by dry etching, any one of alloy materials such as MoCr and MoW, and a conductive material such as WN that have resistance to dry etching needs to be used. In the case of forming the protective members 160 in advance, as illustrated in FIG. 6D, a structure is used, in which, each of the protective members 160 is disposed between the second main electrode 136 and the first electrode 122 under a corresponding one of the contact holes of the interlayer insulating layer 120.

Third Embodiment

Figure 7A:
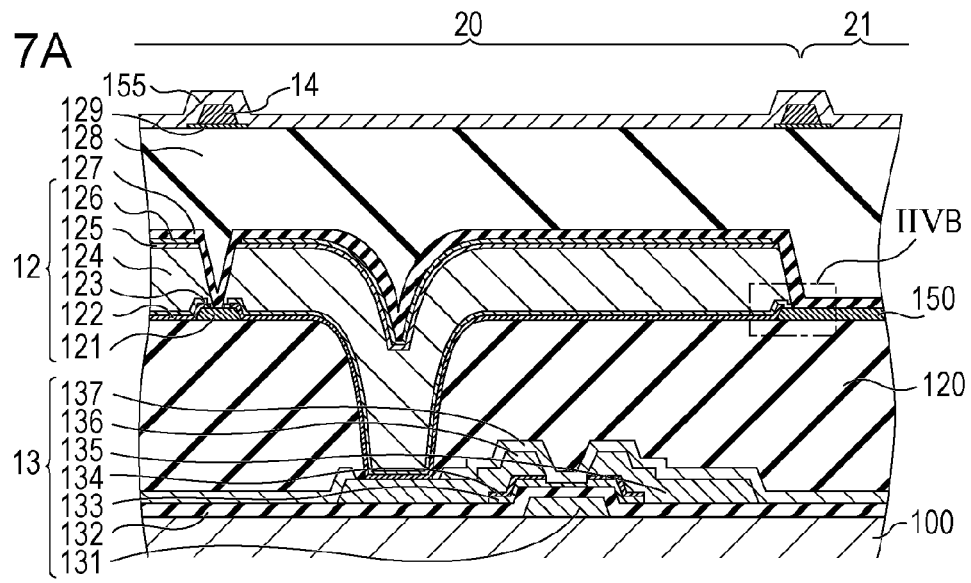
FIGS. 7A to 7C are schematic cross-sectional views of a detection apparatus according to a third embodiment.
Figure 7B:
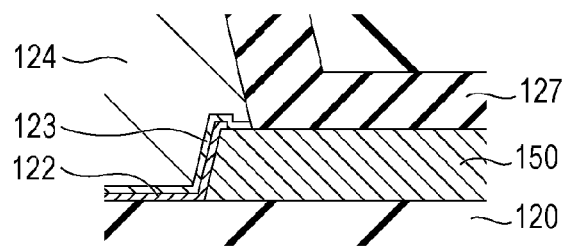
Figure 7C:
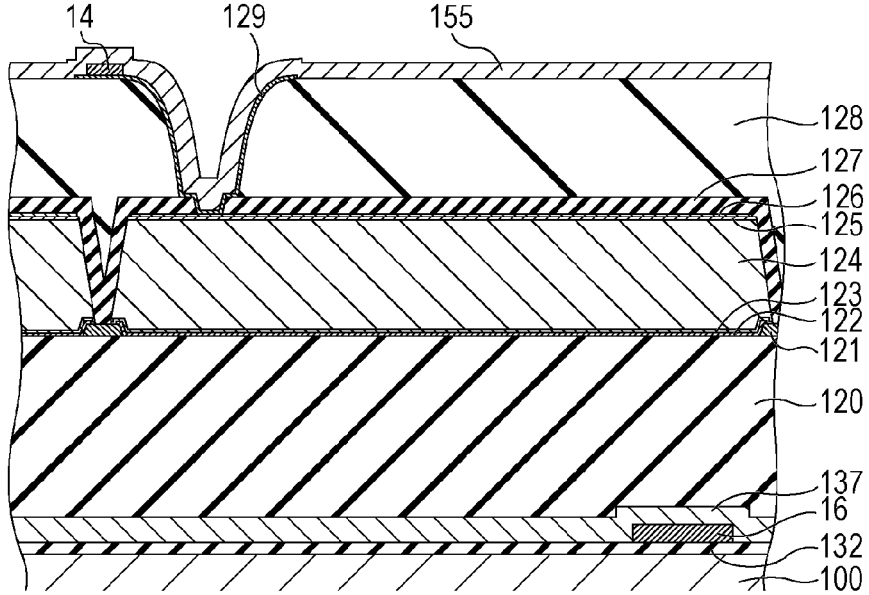

Next, a structure of each pixel included in a detection apparatus according to a third embodiment of the present invention will be described using FIGS. 7A to 7C. FIG. 7A is a schematic cross-sectional view taken along the line A-A in FIG. 1C. FIG. 7B is a schematic cross-sectional view in which a region VIIB in FIG. 7A is enlarged. FIG. 7C is a schematic cross-sectional view taken along the line B-B in FIG. 1C. Furthermore, elements the same as the elements described in the foregoing embodiments are denoted by the same reference numerals, and a detailed description thereof is omitted.

In the first embodiment, ends of the first electrodes 122 are disposed under the covering layer 150. In contrast, in the present embodiment, ends of the first electrodes 122 are disposed between the covering layer 150 and the impurity semiconductor layer 123.

Next, a method for producing the detection device according to the third embodiment of the present invention will be described using FIGS. 8A to 8D. Note that, regarding processes the same as the processes described in the first embodiment, a detailed description thereof is omitted. Note that each of FIGS. 8A and 8C is a schematic plan view of a mask pattern of a photomask used in a corresponding one of the processes for the pixel illustrated in FIG. 1C. Furthermore, each of FIGS. 8B and 8D is a schematic cross-sectional view taken along the line A-A in FIG. 1C in a corresponding one of the processes. Note that, because a process of forming contact holes in the interlayer insulating layer 120 and processes that have been performed before the process is performed are the same as the processes described in the first embodiment, a detailed description thereof is omitted.

First, in the process illustrated in FIG. 8B, an insulating film composed of a typical inorganic material, such as a silicon nitride film or a silicon oxide film, is deposited using a CVD method so as to cover the interlayer insulating layer 120. Then, the covering members 121 and the covering layer 150 are formed using the mask illustrated in FIG. 8A.

Next, in the process illustrated in FIG. 8D, a conductive film composed of Al, ITO, or the like is deposited so as to cover the interlayer insulating layer 120, the covering members 121, and the covering layer 150. Then, the conductive film is subjected to etching using the mask illustrated in FIG. 8C, thereby forming the first electrodes 122 of the conversion elements 12. In this case, the surface of the interlayer insulating layer 120 is covered with the covering members 121, the first electrodes 122, and the covering layer 150. Thus, in the process following the process illustrated in FIG. 8D, in the case of depositing an impurity semiconductor layer, which is to be the impurity semiconductor layer 123, using a CVD method, mixing of the organic material into the first-conductivity-type impurity semiconductor layer due to scattering of the organic material can be reduced. Therefore, occurrence of an image artifact can be reduced. In the present embodiment, the process illustrated in FIG. 8B and the process illustrated in FIG. 8D correspond to the first step of the present invention.

Because the process of depositing the impurity semiconductor layer and processes thereafter, which correspond to the second step, are the same as the processes described as examples in the first embodiment, a description thereof is omitted. Note that, in the present embodiment, an example is described, in which an inorganic insulating film the same as the material that the covering members 121 are formed from is used as the material that covering layer 150 is formed from, and in which the covering members 121 and the covering layer 150 are formed together. However, the present invention is not limited thereto. As described in the first embodiment, even in the present embodiment, another structure and method can be applied.

Figure 9A:
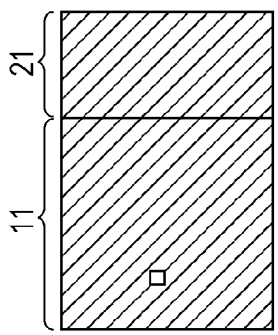
FIGS. 9A and 9C are schematic plan views of mask patterns for explaining an example of another method for producing the detection apparatus according to the third embodiment.

Furthermore, in the present embodiment, a structure may be used, in which only the inner sides of portions that are portions of the protective film 137 and that are to be contact holes are subjected to etching using a mask illustrated in FIG. 9A instead of the mask illustrated in FIG. 8A. In this case, a structure illustrated in FIG. 9B is obtained.

Figure 9B:
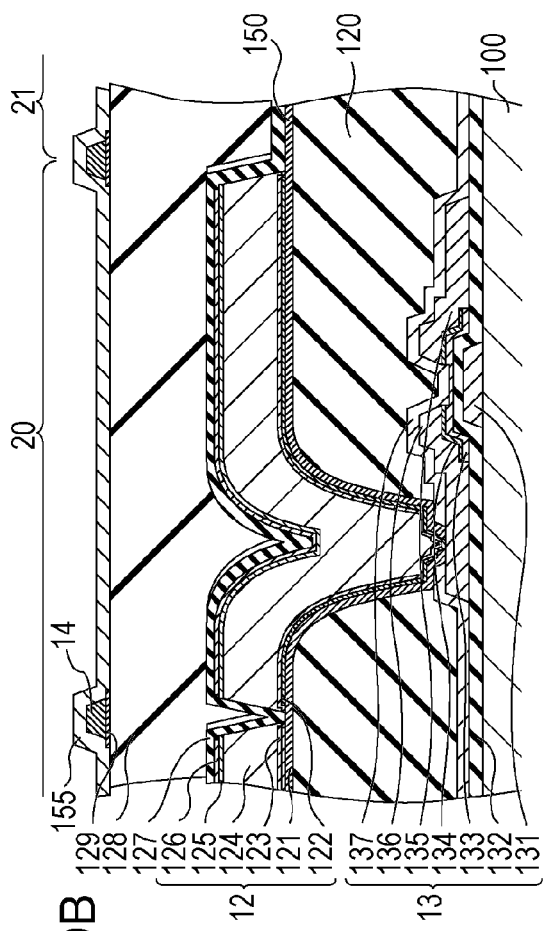
FIGS. 9B and 9D are schematic cross-sectional views of a detection apparatus for explaining the example of another method for producing the detection apparatus according to the third embodiment.
Figure 9C:
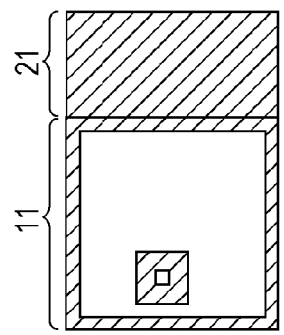

Furthermore, in the present embodiment, without providing contact holes in the protective film 137 in advance, portions of a protective film 137' that are portions to be contact holes and an inorganic insulating film 121' may be subjected to, together, etching using a mask illustrated in FIG. 9C instead of the mask illustrated in FIG. 8A, whereby the contact holes of the protective film 137, the covering members 121, and the covering layer 150 may be formed together. In this case, a structure illustrated in FIG. 9D is obtained.

Figure 9D:
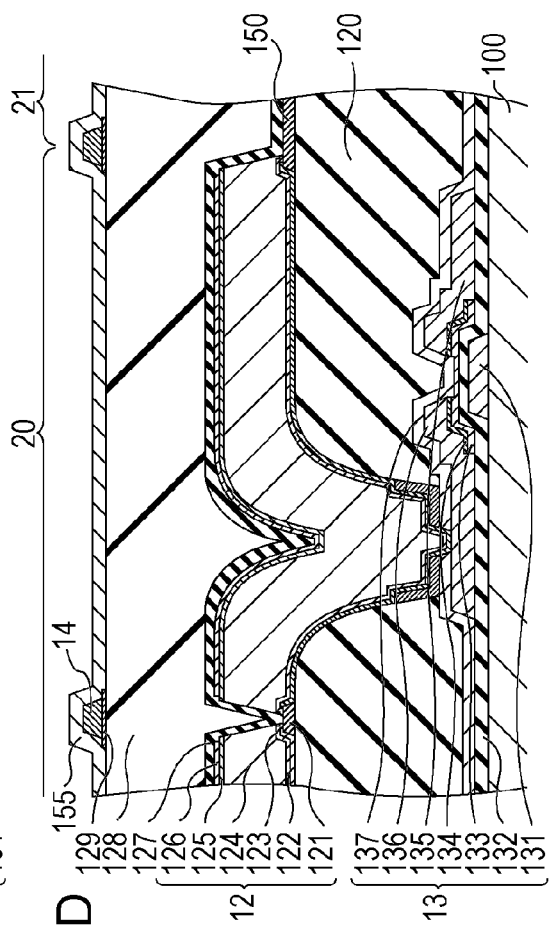

Even with any one of the structures illustrated in FIGS. 9B and 9D, as with the structure illustrated in FIG. 8B, mixing of the organic material into the first-conductivity-type impurity semiconductor layer due to scattering of the organic material can be reduced. Thus, occurrence of an image artifact can be reduced.

Fourth Embodiment

Figure 10A:
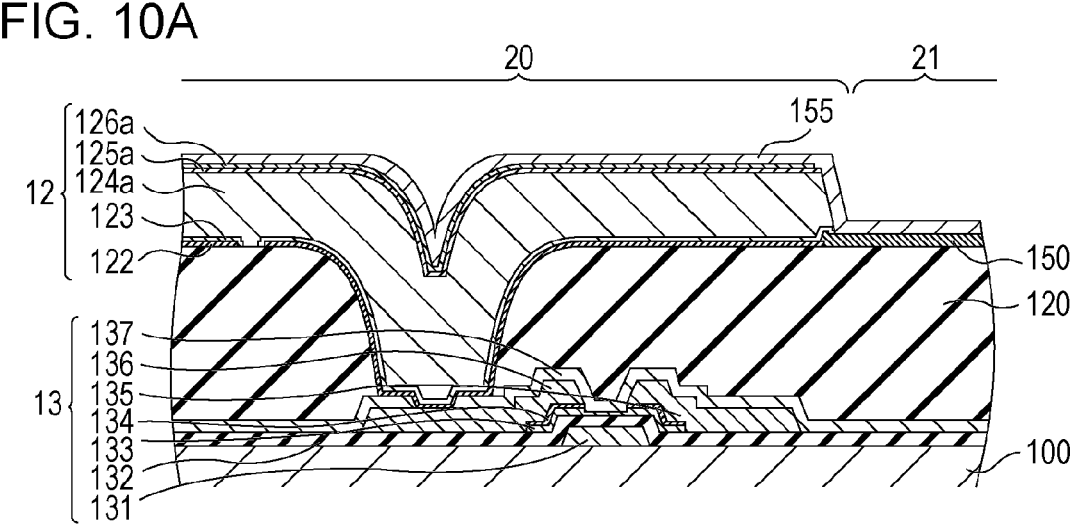
FIGS. 10A and 10C are schematic cross-sectional views of a detection apparatus according to a fourth embodiment.
Figure 10B:
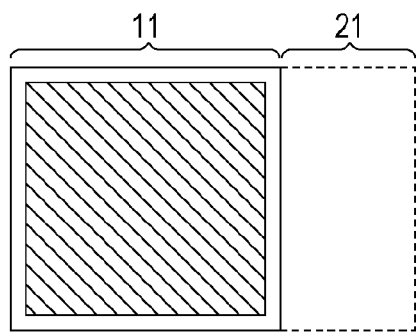
FIG. 10B is a schematic plan view of a mask pattern.
Figure 10C:
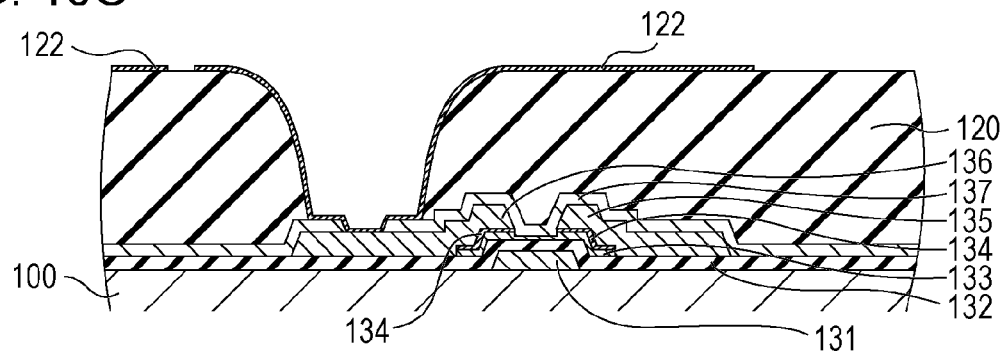

Next, a structure of each pixel included in a detection apparatus according to a fourth embodiment of the present invention will be described using FIGS. 10A to 10C. FIGS. 10A and 10C are cross-sectional views taken along the line A-A in FIG. 1C. Note that FIG. 10B is a schematic plan view of a mask pattern of a photomask used in a process. Note that elements the same as the elements described in the foregoing embodiments are denoted by the same reference numerals, and a detailed description thereof is omitted.

In the first embodiment, the semiconductor layer 124 and the impurity semiconductor layer 125 are separated into pieces on a pixel-by-pixel basis, and the second electrodes 126 are separated from one another on a pixel-by-pixel basis. In contrast, in the present embodiment, as illustrated in FIG. 10A, a semiconductor layer 124a and an impurity semiconductor layer 125a are not separated into pieces on a pixel-by-pixel basis, and second electrodes 126a are not separated from one another on a pixel-by-pixel basis. However, the first electrodes 122 are separated from one another on a pixel-by-pixel basis, and the impurity semiconductor layer 123 are separated into pieces on a pixel-by-pixel basis. Thus, the conversion elements 12 are individualized on a first-electrode-122-by-first-electrode-122 basis. Therefore, in the structure in the present embodiment, the aperture ratio can be increased, compared with that in the structure in the first embodiment. Furthermore, because the second electrodes 126a are not separated from one another on a pixel-by-pixel basis, it is not necessary to provide the electrode wiring patterns 14 that cause the aperture ratio to be reduced. However, in the case where the resistance based on only the resistance of the second electrodes 126a is high, the electrode wiring patterns 14 may be provided. In this case, the semiconductor layer 124a is not separated into pieces on a pixel-by-pixel basis, and the second electrodes 126a are not separated from one another on a pixel-by-pixel basis. Thus, the electrode wiring patterns 14 can be disposed so that the positions of the electrode wiring patterns 14 include positions at which the orthogonal projections of the electrode wiring patterns 14 do not overlap with the impurity semiconductor layer 123. Thus, the electrode wiring patterns 14 can be provided without reducing the aperture ratio. Furthermore, in the present embodiment, the covering members 121 are not provided. Even without the covering members 121, there is no large difference between the degrees of organic contamination of the individual conversion elements 12. Thus, an image artifact does not become a problem. The same is also true in the other embodiments of the present invention.

Next, a method for producing the detection apparatus according to the fourth embodiment of the present invention will be described using FIGS. 11A to 11H. Note that each of FIGS. 11A, 11C, 11E, and 11G is a schematic plan view of a mask pattern of a photomask used in a corresponding one of processes. Furthermore, each of FIGS. 11B, 11D, 11F, and 11H is a schematic cross-sectional view taken along the line A-A in FIG. 1C in a corresponding one of the processes. Note that, regarding processes the same as the processes described in the first embodiment, a detailed description thereof is omitted. More specifically, a process of forming the first electrodes 122 and processes that have been performed before the process is performed are the same as the processes described using FIGS. 3A to 3D. Thus, processes thereafter will be described.

First, in the process illustrated in FIG. 11B, a film composed of a typical inorganic material, such as a silicon nitride film or a silicon oxide film, is deposited so as to cover the interlayer insulating layer 120 and the first electrodes 122. Then, in the pixel-array outside region 21, the covering layer 150 is formed using the mask illustrated in FIG. 9A. In this case, the interlayer insulating layer 120 is exposed at most only between the multiple first electrodes 122. The exposed area of the interlayer insulating layer 120 between the first electrodes 122 is at most within 20% of the total area of the interlayer insulating layer 120 per pixel, and is much smaller than the area of the interlayer insulating layer 120 in the pixel-array outside region 21. Thus, the exposure of the interlayer insulating layer 120 is not a factor causing organic contamination, for example, that results in occurrence of an image artifact. Note that the covering layer 150 may completely cover the surface of the interlayer insulating layer 120 in the pixel-array outside region 21. Alternatively, the covering layer 150 may not completely cover the surface of the interlayer insulating layer 120 if the exposed area of the surface of the interlayer insulating layer 120 in the pixel-array outside region 21 is almost equal to that of the surface of the interlayer insulating layer 120 in the pixel-array region 20. The same is also true in the other embodiments of the present invention. In the present embodiment, the process illustrated in FIG. 11B corresponds to the first step of the present invention.

Next, in the process illustrated in FIG. 11D, an amorphous silicon film in which a pentavalent element, such as phosphorus, is implanted as an impurity is deposited as the first-conductivity-type impurity semiconductor film 123' using a plasma CVD method or the like so as to cover the covering layer 150 and the first electrodes 122. Then, one portion of the impurity semiconductor film 123' is removed by dry etching using the mask illustrated in FIG. 11C, thereby forming the impurity semiconductor layer 123.

Next, in the process illustrated in FIG. 11F, an amorphous silicon film is deposited as the semiconductor film 124' using a plasma CVD method or the like so as to cover the covering layer 150 and the impurity semiconductor layer 123. Next, an amorphous silicon film in which a trivalent element, such as boron, is implanted as an impurity is deposited as the second-conductivity-type impurity semiconductor film 125' using a plasma CVD method or the like.

Next, a transparent conductive oxide film 126' is deposited using a sputtering method so as to cover the impurity semiconductor film 125'. Then, the transparent conductive oxide film 126' is subjected to wet etching using the mask illustrated in FIG. 11E, thereby forming the second electrodes 126a.

Next, in the process illustrated in FIG. 11H, the impurity semiconductor film 125' and the semiconductor film 124' in the pixel-array outside region 21 are subjected to dry etching using the mask illustrated in FIG. 11G, thereby forming an impurity semiconductor layer 125a and a semiconductor layer 124a.

Next, the passivation layer 155 is formed so as to cover the second electrodes 126a and the covering layer 150, thereby obtaining the structure illustrated in FIG. 10A. In the present embodiment, the process illustrated in FIG. 11D, the process illustrated in FIG. 11F, and the process illustrated in FIG. 11H correspond to the second step of the present invention.

Note that, also in the present embodiment, the covering members 121 may be disposed between the first electrodes 122.

Furthermore, also in the present embodiment, as described in the second embodiment, the protective members 160 may be disposed in the contact holes of the interlayer insulating layer 120. Furthermore, also in the present embodiment, as in the third embodiment, a structure in which ends of the first electrodes 122 are disposed between the covering layer 150 and the impurity semiconductor layer 123 may be used.

Application Embodiment

Next, a radiation detection system using the detection apparatus according to any one of the embodiments of the present invention will be described using FIG. 12.

Figure 12:
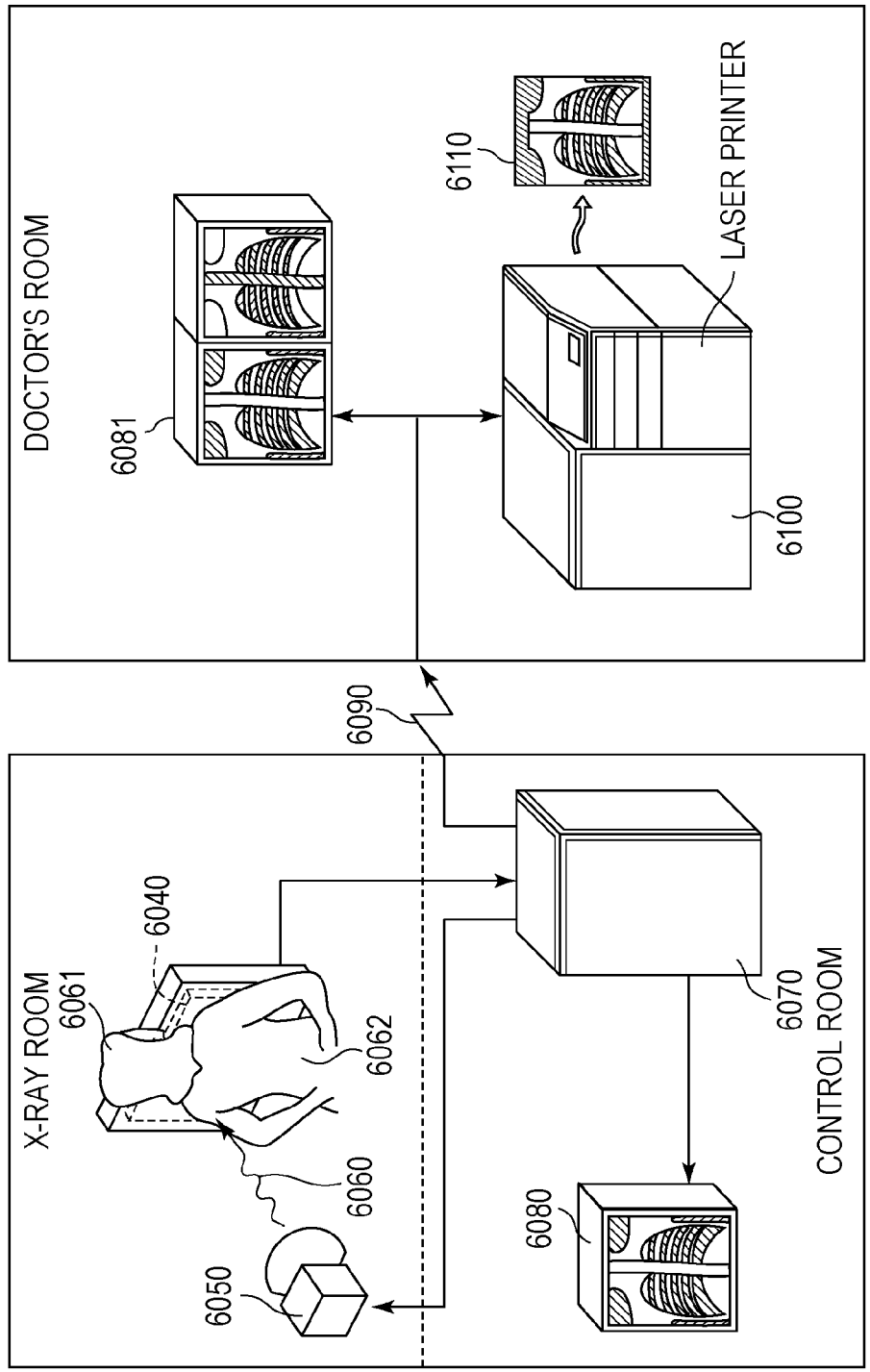
FIG. 12 is a schematic diagram of a radiation detection system using the detection apparatus according to any one of the embodiments of the present invention.

As illustrated in FIG. 12, X-rays 6060 generated by an X-ray tube 6050 that is a radiation source pass through a body part 6062 of a patient or subject 6061, and enter individual conversion elements included in a radiation detection apparatus 6040. Information concerning the inside of the body of the patient 6061 is included in the X-rays that have entered the conversion elements. Radiation is converted into electric charges by a conversion unit 3 (FIG. 5) on the basis of the X-rays that have entered the conversion elements, thereby obtaining electric information. This information is converted into digital data, subjected to image processing by an image processor 6070 that is a signal processing unit, and can be monitored on a display screen 6080 that is a display unit of a control room.

Furthermore, this information can be transferred to a remote location by a transmission processing unit such as a wired or wireless network 6090, and can be displayed on a display screen 6081 that is a display unit or stored in a recording unit such as an optical disk, for example, at another place such as a doctor's room. A doctor in the remote location can make a diagnosis. Furthermore, the information can be recorded, by a film processor 6100 that is a recording unit, in a film 6110 that is a recording medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-220385 filed Oct. 2, 2012, which is hereby incorporated by reference herein in its entirety.

What is claimed is:

1. A method for producing a detection apparatus, the detection apparatus including a pixel-array region where a plurality of pixels is disposed on a substrate and a pixel-array outside region disposed outside the pixel-array region on the substrate, each of the plurality of pixels including a conversion elements including an electrode electrically connected to a corresponding one of a plurality of switching elements, an impurity semiconductor layer disposed on the electrode, and a semiconductor layer disposed on the impurity semiconductor layer, the method comprising:

a first step of forming a plurality of electrodes in the pixel-array region on a surface of an interlayer insulating layer formed so as to cover the plurality of switching elements, and forming a covering layer on a surface of the interlayer insulating layer in the pixel-array outside region, the covering layer being composed of an inorganic material; and a second step of forming the impurity semiconductor layer on the electrodes so that an end of the impurity semiconductor layer of a pixel located at an edge of the pixel-array region among the plurality of pixels is laid on the covering layer.

2. The method for producing a detection apparatus according to claim 1, wherein the first step further includes a step of depositing a conductive film so as to cover the interlayer insulating layer and forming the electrodes from the conductive film, and a step of depositing a film so as to cover the interlayer insulating layer and the electrodes and forming the covering layer from the film, the film being composed of an inorganic material.

3. The method for producing a detection apparatus according to claim 1, wherein the first step further includes a step of depositing a film so as to cover the interlayer insulating layer and forming the covering layer from the film, the film being composed of an inorganic material, and a step of depositing a conductive film so as to cover the interlayer insulating layer and the covering layer and forming the electrodes from the conductive film.

4. The method for producing a detection apparatus according to claim 1, wherein the second step further includes a step of depositing an impurity semiconductor film, which is to be an impurity semiconductor layer so as to cover the electrodes and the covering layer, a step of forming the impurity semiconductor layer in such manner that one portion of the impurity semiconductor film is removed on the covering layer, and a step of depositing a semiconductor film, which is to be the semiconductor layer, so as to cover the impurity semiconductor layer.

5. The method for producing a detection apparatus according to claim 1, wherein the second step further includes a step of depositing an impurity semiconductor film, which is to be an impurity semiconductor layer so as to cover the electrodes and the covering layer, a step of depositing a semiconductor film, which is to be the semiconductor layer, so as to cover the impurity semiconductor film, and a step of forming the impurity semiconductor layer from the impurity semiconductor film and the semiconductor layer of the conversion elements from the semiconductor film in such a manner that one portion of the impurity semiconductor film and one portion of the semiconductor film, respectively, are removed on the covering layer.

6. The method for producing a detection apparatus according to claim 4, wherein the second step further includes a step of depositing an impurity semiconductor film, which has a conductivity type different from that of the impurity semiconductor film, so as to cover the semiconductor film, a step of depositing a conductive film, which is to be other electrodes of the conversion elements that are different from the electrodes, so as to cover the impurity semiconductor film having a different conductivity type, and a step of forming electrode wiring patterns at positions at which the orthogonal projections of the electrode wiring patterns overlap with the covering members, the electrode wiring patterns and the conductive film having junctions therebetween.

7. The method for producing a detection apparatus according to claim 5, wherein the second step further includes a step of depositing an impurity semiconductor film, which has a conductivity type different from that of the impurity semiconductor film, so as to cover the semiconductor film, a step of depositing a conductive film, which is to be other electrodes of the conversion elements that are different from the electrodes, so as to cover the impurity semiconductor film having a different conductivity type, and a step of forming electrode wiring patterns at positions at which the orthogonal projections of the electrode wiring patterns overlap with the covering members, the electrode wiring patterns and the conductive film having junctions therebetween.

8. The method for producing a detection apparatus according to claim 1, wherein the first step further includes a step of forming covering members so that the covering members are disposed between the electrodes in the pixel-array region so as to cover the interlayer insulating layer and composed of an inorganic material, and a step of forming the covering layer on the pixel-array outside region.

9. The method for producing a detection apparatus according to claim 8, wherein the covering layer and the covering members are formed from the same film.

10. The method for producing a detection apparatus according to claim 1,
wherein the plurality of switching elements are thin film transistors disposed on a substrate,
wherein the interlayer insulating layer has contact holes used to electrically connect main electrodes of the thin film transistors and the electrodes, and
wherein the first step further includes a step of forming protective members configured to protect the main electrodes in the contact holes.

11. The method for producing a detection apparatus according to claim 1,
wherein the inorganic material is an inorganic insulating material.

* * * * *